(12) United States Patent
Newman

(10) Patent No.: US 8,834,916 B2
(45) Date of Patent: Sep. 16, 2014

(54) APPARATUS AND METHOD FOR REMOVING EPITHELIUM FROM THE CORNEA

(75) Inventor: Leonard Newman, Orinda, CA (US)

(73) Assignee: Leonard A. Newman, Orinda, CA (US)

( * ) Notice: Subject to any disclaimer, the term of this patent is extended or adjusted under 35 U.S.C. 154(b) by 162 days.

(21) Appl. No.: 12/901,846

(22) Filed: Oct. 11, 2010

(65) Prior Publication Data

US 2012/0087970 A1    Apr. 12, 2012

(51) Int. Cl.
*A61F 2/00* (2006.01)
*A61F 2/14* (2006.01)
*A61K 31/525* (2006.01)
*A61F 9/013* (2006.01)
*A61K 9/00* (2006.01)

(52) U.S. Cl.
CPC ............ *A61K 31/525* (2013.01); *A61F 9/013* (2013.01); *A61K 9/0051* (2013.01)
USPC .......................... 424/427; 623/5.11; 623/5.16

(58) Field of Classification Search
CPC ... A61F 2/142; A61F 2/14; A61F 2250/0067; A61F 2/145
USPC ................................. 424/427; 623/5.11, 5.16
See application file for complete search history.

(56) References Cited

U.S. PATENT DOCUMENTS 3,993,071 A * 11/1976 Higuchi et al. ............... 424/428
5,347,326 A *  9/1994 Volk .......................... 351/159.02
2004/0043082 A1 *  3/2004 Karageozian et al. ........ 424/710

OTHER PUBLICATIONS

Helena, M. C.; Filatov, V. V.; Johnston, W. T.; Vidaurri-Leal, J.; Wilson, S. E.; Talamo, J. H. Cornea, 1997, v. 16, iss. 5, Abstract.*

* cited by examiner

*Primary Examiner* — Abigail Fisher

(57) ABSTRACT

An apparatus and a method for removing epithelium from the cornea include a fluid agent for facilitating de-epithelialization of the cornea. A disc includes a biocompatible material operable for covering a predetermined zone of a cornea. The disc is hydrated by the fluid agent, wherein the hydrated disc is pliable for conforming to a surface of the cornea. An application of the hydrated disc to the cornea substantially constrains the fluid agent to the determined zone and softens a corneal epithelium enabling delamination of the epithelium from an underlying stroma.

20 Claims, 3 Drawing Sheets

US 8,834,916 B2

APPARATUS AND METHOD FOR REMOVING EPITHELIUM FROM THE CORNEA

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

FIELD OF THE INVENTION

The present invention relates generally to ophthalmology. More particularly, the invention relates to an apparatus and method for removing epithelium from the cornea.

BACKGROUND OF THE INVENTION

Photorefractive Keratotomy is corrective eye surgery that utilizes an excimer laser to change the curvature of the cornea in an effort to correct myopia, hyperopia and astigmatism. Lately, more complex ablation patterns have allowed for the correction of higher order aberrations. A fundamental step during the surgery is symmetric, rapid removal of the central and paracentral corneal epithelium, or skin layer of the cornea, to enable the laser to reshape the corneal stroma. The more consistent a surgeon becomes at this step, the more consistent his or her results will be. The ultimate goal is to remove enough of the epithelium to support the larger diameter of modern day excimer lasers yet not too much as this prolongs the healing time and may increase the risk of infection. Removal of the epithelium can be a very stressful part of the procedure from a patient's perspective, and minimizing the patient's anxiety can improve their ability to follow the surgeon's instructions and maximize the success of the surgical outcome. It is therefore an objective of the present invention to provide means for removing the corneal epithelium that is consistent and less stressful to the patient.

Current techniques and devices used to remove the epithelium include rotating brushes similar to an electric toothbrush that grind away the epithelium. These brushes can pull the eye in different directions adding stress to the patient and may remove too much of the epithelium. Another current technique involves holding a small well on the patient's eye that contains an agent to weaken the epithelium's adhesion to the underlying stroma. This technique can also be stressful to the patient as the surgeon must place a certain amount of pressure on the eye to contain the agent, and if the patient moves their eye, the agent can spill over the eye causing the surgeon to spend additional time cleaning up the spill, which increases surgical time and makes results less consistent. Spillage can also lead to more chronic problems such as, but not limited to, dry eye. Another current epithelial removal technique involves using a sharp blade to debride the epithelium which can cause an irregular surface and ultimately may limit the surgical result.

In view of the foregoing, there is a need for improved techniques for removing the corneal epithelium that enables a user to control the amount of the epithelium that is removed, minimizes the risk of spillage and creates an even surface.

BRIEF DESCRIPTION OF THE DRAWINGS

The present invention is illustrated by way of example, and not by way of limitation, in the figures of the accompanying drawings and in which like reference numerals refer to similar elements and in which.

Figure 1:
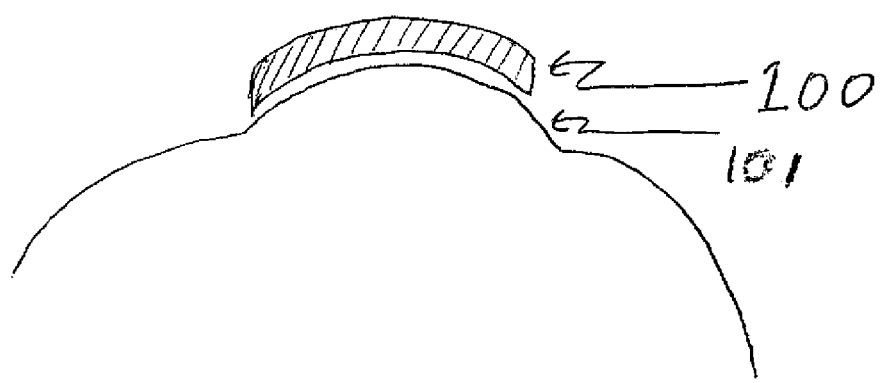
FIG. 1 is a cross sectional side view of an exemplary epithelium removal disc on a cornea, in accordance with an embodiment of the present invention.

Unless otherwise indicated illustrations in the figures are not necessarily drawn to scale.

SUMMARY OF THE INVENTION

To achieve the forgoing and other objects and in accordance with the purpose of the invention, a variety of apparatuses and methods for removing epithelium from the cornea are presented.

In one embodiment an apparatus includes means for facilitating de-epithelialization of the cornea, and means for covering a predetermined zone of a cornea, the covering means being hydrated by the facilitating means, wherein the hydrated covering means conforms to a surface of the cornea, and softens a corneal epithelium enabling delamination of the epithelium from an underlying stroma. Another embodiment further includes means for containing the covering means.

In another embodiment an apparatus includes a fluid agent for facilitating de-epithelialization of the cornea. A disc includes a biocompatible material operable for covering a predetermined zone of a cornea. The disc is hydrated by the fluid agent, wherein the hydrated disc is pliable for conforming to a surface of the cornea. An application of the hydrated disc to the cornea substantially constrains the fluid agent to the determined zone and softens a corneal epithelium enabling delamination of the epithelium from an underlying stroma. Another embodiment further includes a sterile packet for containing at least the disc. In yet another embodiment the fluid agent comprises isopropyl alcohol. In still another embodiment the biocompatible material comprises a hydroxylated polyvinyl acetate material. In another embodiment a concentration level of the isopropyl alcohol is at least in part determined by a desired application time and an ability of the combination of the isopropyl alcohol and the hydroxylated polyvinyl acetate material to create a moldable fluid matrix having the pliability to mold to the cornea. In yet another embodiment the delamination of the epithelium is substantially symmetrical. In still another embodiment the disc further comprises a hollowed center for application of an additional agent. In another embodiment the additional agent comprises a riboflavin solution or antibiotics. In yet another embodiment the disc further comprises a curved surface generally matching a curve of the cornea. In still another embodiment the disc further comprises a rigid top layer. In another embodiment the disc further comprises a nub on a top surface for aiding in moving the disc.

In another embodiment a method includes the steps of applying to a cornea a disc comprising a biocompatible material having a diameter for covering a predetermined zone of the cornea. The disc is hydrated by a fluid agent for facilitating de-epithelialization of the cornea. The hydrated disc is pliable for conforming to a surface of the cornea, wherein the application of the hydrated disc to the cornea substantially constrains the fluid agent to the predetermined zone and softens a corneal epithelium. The hydrated disc is removed after a period of time, thereby enabling delamination of the epithelium from an underlying stroma. Another embodiment further includes the step of moving the hydrated disc around the cornea using a nub on a top surface of the disc. In yet another embodiment the period of time is at least in part determined by a concentration of the fluid agent. In still another embodiment the fluid agent comprises isopropyl alcohol. In another embodiment the biocompatible material comprises a hydroxylated polyvinyl acetate material. In yet another embodiment a concentration level of the isopropyl alcohol is at least in part determined by an ability of the combination of the isopropyl alcohol and the hydroxylated polyvinyl acetate material to create a moldable fluid matrix having the pliability to mold to the cornea. In still another embodiment the delamination of the epithelium is substantially symmetrical.

Other features, advantages, and objects of the present invention will become more apparent and be more readily understood from the following detailed description, which should be read in conjunction with the accompanying drawings.

DETAILED DESCRIPTION OF THE PREFERRED EMBODIMENTS

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will now be described in detail with reference to embodiments thereof as illustrated in the accompanying drawings.

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present Application or of any further Application derived therefrom.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

Detailed descriptions of the preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

It is to be understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

Some preferred embodiments of the present invention and at least some variations thereof provide an apparatus and method for epithelial removal of the cornea. Some preferred embodiments comprise a disc made of a pliable material containing an agent which facilitates the removal of corneal epithelium by molding to the corneal curvature. Many preferred embodiments provide a surgeon with good control of the amount of epithelium he or she is removing based on the diameter of the disc and remove the epithelium in a homologous manner thereby maintaining consistent hydration of the cornea which maximizes the visual result while minimizing recovery time and risk of infection.

FIG. 1 is a cross sectional side view of an exemplary epithelium removal disc 100 on a cornea 101, in accordance with an embodiment of the present invention. In the present embodiment, disc 100 is preferably made of Merocel®, which is hydroxylated polyvinyl acetate sponge material, with a diameter of approximately 7 mm and a thickness of approximately 0.5 mm. The diameter of disc 100 may vary according to the desired diameter of epithelium to be removed and range from 1 mm to 12 mm depending on the surgical procedure or ablation zone selected. The thickness of disc 100 may also vary from 0.1 mm to 6 mm though a disc of 0.5 mm to 1 mm thickness is optimal as is contains adequate amounts of alcohol and remains suitably pliable to mold the corneal curvature. Also, those skilled in the art will readily recognize, in accordance with the teachings of the present invention, that discs in alternate embodiments may be made of various different types of moldable material such as, but not limited to, silicone or other biocompatible materials or may be made of more rigid materials including, but not limited to, cellulose sponges, silicone, polyvinyl pyrrolidinone based hydrogel, sterile gauze, fibrous materials or paper products. The discs in various alternate embodiments may be made of either hydrophobic or hydrophilic materials. Merocel is preferable because it is "lint free" which is important for eye surgery.

In the present embodiment, disc 100 is hydrated with 70% isopropyl alcohol. At this concentration level, the combination of alcohol and Merocel material together create a moldable fluid matrix to match to the curvature of the cornea. Various concentrations of alcohol can be used with higher concentrations providing a more rapid de-epithelialization which may be preferable to a more experienced surgeon. Hydrating disc 100 with the alcohol enables the Merocel material to become pliable so that it is able to mold to the curvature of cornea 101. This aspect is very important because it provides the surgeon with good control over where and for how long the alcohol solution comes into contact with cornea 101 to distribute the appropriate amount solution over the appropriate portion of cornea 101. Other concentrations of isopropyl alcohol ranging from 5% to 99% may be used in alternate embodiments; however, lower concentrations are required to remain on the eye for a longer period of time and higher concentrations may not enable the disc to mold as well to the cornea. A concentration of 99% isopropyl alcohol is not suitable for a disc made of PVA or methylcellulose as they does not absorb the alcohol well which prevents them from becoming suitably pliable to mold to the curvature of the cornea. Various embodiments would allow for different materials which would become pliable and mold to the corneal curvature with 99% isopropyl alcohol or other agents which would facilitate de-epithelialization of the cornea. In the present embodiment, disc 100 must remain adequately hydrated to function properly. A more rigid disc that does not require as much hydration may be used in an alternate embodiment if it has a curve similar to a human cornea, as shown by way of example in FIG. 3B.

In typical use of the present embodiment, a user places disc 100 on cornea 101, and disc 100 molds to fit the curvature of cornea 101. Disc 100 remains on cornea 101 for approximately 7 seconds and is then removed. The surgeon may choose to keep disc 100 on cornea 101 for a longer or shorter amount of time (ranging from 5 seconds to 30 seconds) depending on factors such as, but not limited to, the concentration of the alcohol solution or the amount of the epithelium that is to be removed. Shorter application times are preferable as they are less stressful to the patient which likely enables them to better follow physician instructions and maximize their surgical outcome. After disc 100 is removed from cornea 101, the surgeon is able to delaminate the epithelium from the underlying stroma in a way that is very low stress to the patient. Furthermore, there is minimal spillage of the alcohol solution even if the patient inadvertently moves their eye as disc 100 keeps the alcohol solution contained. These two elements can help maximize the end result of the surgery as the spillage of the alcohol solution causes the surgeon to spend additional time cleaning up the spill, which increases surgical time and makes results less consistent and can lead to more chronic problems such as, but not limited to, dry eye. Disc 100 also enables the surgeon to control where the alcohol solution is distributed on cornea 101 since the alcohol solution does not spread past the diameter of disc 100, and this controlled distribution allows for the symmetric removal of the epithelium. Disc 100 is very easy to use and effective for even the most inexperienced surgeon. The technique of using disc 100 in accordance with the present embodiment is quick, easy, low stress to the patient and allows for good control of the area treated by the surgeon. In alternate applications, disc 100 may be used to deliver other medications or chemicals to the surface of the eye.

Disc 100 is preferably provided to surgeons in a sterile packet similar to alcohol hand wipes or alcohol wipes used in hospitals to clean the skin before drawing blood, etc. A technician can open the packet immediately prior to use to maintain the hydration of disc 100 with the alcohol solution since disc 100 looses its effectiveness as the alcohol evaporates. Alternate embodiments comprising different solutions used to de-epithelialize the cornea or to deliver medication may also be packaged in a sterile packet for easy use. Alternatively, the disc may be packaged in the packet dry and the solution may be added after the packet is opened immediately prior to use, or the disc may not be packaged in a packet.

Figure 2:
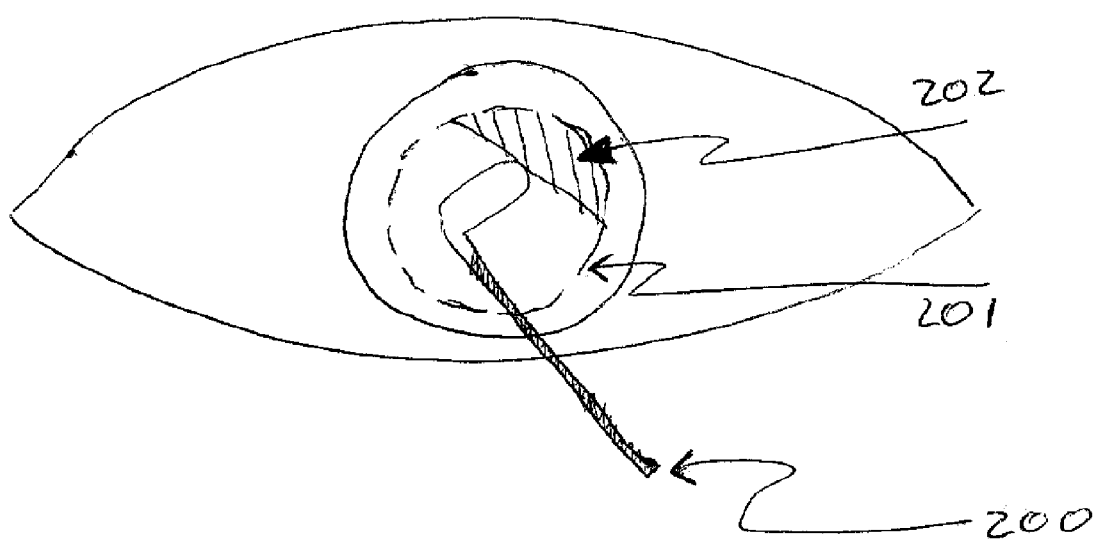
FIG. 2 is a diagrammatic top view of an exemplary surgical spatula removing a portion of epithelium that has been weakened by a removal solution from a cornea, in accordance with an embodiment of the present invention.

FIG. 2 is a diagrammatic top view of an exemplary surgical spatula 200 removing a portion of epithelium 202 that has been weakened by a removal solution from a cornea, in accordance with an embodiment of the present invention. After the removal solution soaks epithelium 202 through an epithelium removal disc, as described by way of example in accordance with FIG. 1, and the removal disc is taken off of the cornea, a surgeon can implement surgical spatula 200 to scrape off epithelium 202. Epithelium 202 is weakened from the application of the removal solution in an area 201 equal in size to the diameter of the epithelium removal disc used. Alternatively, the surgeon may use a variety of readily available instruments to remove the epithelium such as, but not limited to, other relatively blunt instruments, a polyvinyl acetate (PVA) or methylcellulose Lasik surgical spear, or a rotating brush.

Figure 3A:
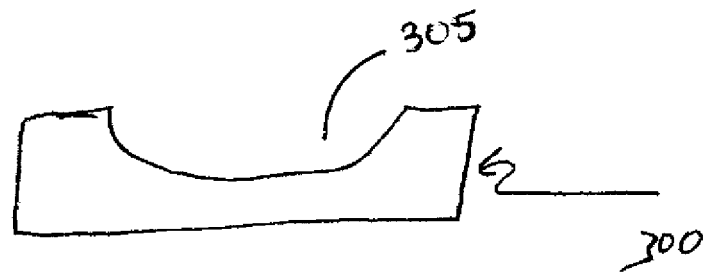
FIGS. 3A through 3D are cross sectional side views of various different implementations of exemplary epithelium removal discs, in accordance with embodiments of the present invention.
Figure 3B:
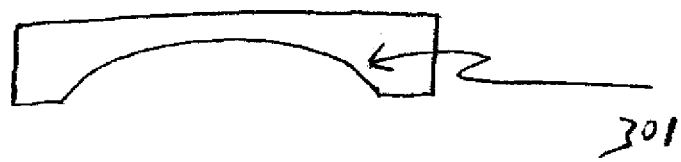
Figure 3C:
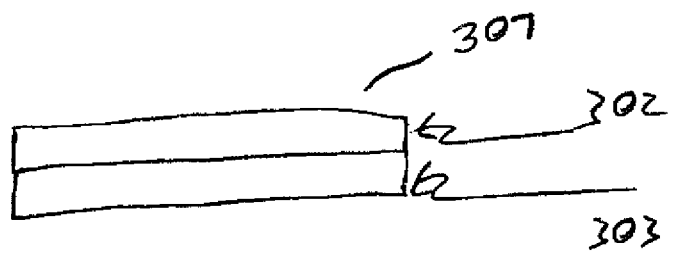
Figure 3D:

FIGS. 3A through 3D are cross sectional side views of various different implementations of exemplary epithelium removal discs, in accordance with embodiments of the present invention. Referring to FIG. 3A, a disc 300 comprises a hollow center 305 that may be filled with a denaturing solution for epithelial removal. This hollow center may also be filled with various other chemicals to potentially treat infection or penetrate more deeply into the corneal stroma such as, but not limited to, riboflavin solution for collagen cross linking or antibiotics. Referring to FIG. 3B, a disc 301 is made of a rigid or semi rigid material such as, but not limited to, fibrous materials, silicone, polyvinyl pyrrolidinone based hydrogel, or nylon. Because of the rigidity of disc 301, disc 301 has a curve similar to a human cornea in order to fit properly on a cornea. Referring to FIG. 3C a disc 307 is made of a more rigid layer 302 with a softer more pliable base 303. Base 303 can conform to the curvature of a cornea. Referring to FIG. 3D, a disc 309 comprises a small grab handle or nub 304 to aid in moving disc 309 around an eye.

Those skilled in the art will readily recognize, in accordance with the teachings of the present invention, that alternate embodiments may be implemented in different ways For example, without limitation, the disc in some alternate embodiments may comprise a color or physical identifier to differentiate it from other sponges on the surgical tray. In another alternate embodiment, the disc may be used in conjunction with a rotating brush for epithelial removal. In other alternate embodiments, the disc may start with a specific diameter and then enlarge, shrink or remain at a specific size once hydrated. The sizing of these embodiments is based on the size of the ablation zone.

Having fully described at least one embodiment of the present invention, other equivalent or alternative methods of providing means for epithelium removal according to the present invention will be apparent to those skilled in the art. The invention has been described above by way of illustration, and the specific embodiments disclosed are not intended to limit the invention to the particular forms disclosed. For example, the particular implementation of the disc may vary depending upon the particular type of application for which it is used. The discs described in the foregoing were directed to corneal epithelium removing implementations; however, similar techniques are to provide epithelium removing discs for different areas of the body in both human and veterinary medicine including, but not limited to, the sclera, mouth, etc. Non-corneal epithelium removing implementations of the present invention are contemplated as within the scope of the present invention. The invention is thus to cover all modifications, equivalents, and alternatives falling within the spirit and scope of the following claims.

Claim elements and steps herein may have been numbered and/or lettered solely as an aid in readability and understanding. Any such numbering and lettering in itself is not intended to and should not be taken to indicate the ordering of elements and/or steps in the claims.

What is claimed is:

1. An apparatus comprising:
   means for facilitating de-epithelialization of the cornea; and
   means for covering a predetermined zone of a cornea, said covering means being hydrated by said facilitating means, wherein said hydrated covering means conforms to a surface of the cornea, and softens a corneal epithelium enabling delamination of the epithelium from an underlying stroma.

2. The apparatus as recited in claim 1, further comprising means for containing said covering means.

3. An apparatus comprising:
   a fluid agent for facilitating de-epithelialization of the cornea; and
   a disc comprising a biocompatible material operable for covering a predetermined zone of a cornea, said disc being hydrated by said fluid agent, wherein said hydrated disc is pliable for conforming to a surface of the cornea, and an application of said hydrated disc to the cornea substantially constrains said fluid agent to said determined zone and softens a corneal epithelium enabling delamination of the epithelium from an underlying stroma.

4. The apparatus as recited in claim 3, further comprising a sterile packet for containing at least said disc.

5. The apparatus as recited in claim 3, wherein said fluid agent comprises isopropyl alcohol.

6. The apparatus as recited in claim 5, wherein said biocompatible material comprises a hydroxylated polyvinyl acetate material.

7. The apparatus as recited in claim 6, wherein a concentration level of said isopropyl alcohol is at least in part determined by a desired application time and an ability of the combination of said isopropyl alcohol and said hydroxylated polyvinyl acetate material to create a moldable fluid matrix having the pliability to mold to the cornea.

8. The apparatus as recited in claim 3, wherein said delamination of the epithelium is substantially symmetrical.

9. The apparatus as recited in claim 3, wherein said disc further comprises a hollowed center for application of an additional agent.

10. The apparatus as recited in claim 9, wherein said additional agent comprises a riboflavin solution or antibiotics.

11. The apparatus as recited in claim 3, wherein said disc further comprises a curved surface generally matching a curve of the cornea.

12. The apparatus as recited in claim 3, wherein said disc further comprises a rigid top layer.

13. The apparatus as recited in claim 3, wherein said disc further comprises a nub on a top surface for aiding in moving said disc.

14. A method comprising the steps of:
   applying to a cornea a disc comprising a biocompatible material operable for covering a predetermined zone of the cornea, said disc being hydrated by a fluid agent for facilitating de-epithelialization of the cornea, and said hydrated disc is pliable for conforming to a surface of the cornea, wherein the application of said hydrated disc to the cornea substantially constrains said fluid agent to said predetermined zone and softens a corneal epithelium; and removing said hydrated disc after a period of time, thereby enabling delamination of the epithelium from an underlying stroma.

15. The method as recited in claim 14, further comprising the step of moving said hydrated disc around the cornea using a nub on a top surface of said disc.

16. The method as recited in claim 14, wherein said period of time is at least in part determined by a concentration of said fluid agent.

17. The method as recited in claim 14, wherein said fluid agent comprises isopropyl alcohol.

18. The method as recited in claim 17, wherein said biocompatible material comprises a hydroxylated polyvinyl acetate material.

19. The method as recited in claim 18, wherein a concentration level of said isopropyl alcohol is at least in part determined by an ability of the combination of said isopropyl alcohol and said hydroxylated polyvinyl acetate material to create a moldable fluid matrix having the pliability to mold to the cornea.

20. The method as recited in claim 14, wherein said delamination of the epithelium is substantially symmetrical.

* * * * *